(12) United States Patent
Barth et al.

(10) Patent No.: US 7,781,471 B2
(45) Date of Patent: Aug. 24, 2010

(54) DIARYL TRIAZOLMETHYLAMINE DERIVATIVES, PREPARATION AND THERAPEUTIC USE THEREOF

(75) Inventors: Francis Barth, Antony (FR); Murielle Rinaldi-Carmona, Antony (FR)

(73) Assignee: Sanofi-Aventis, Paris (FR)

( * ) Notice: Subject to any disclaimer, the term of this patent is extended or adjusted under 35 U.S.C. 154(b) by 245 days.

(21) Appl. No.: 12/125,297

(22) Filed: May 22, 2008

(65) Prior Publication Data

US 2008/0293794 A1 Nov. 27, 2008

Related U.S. Application Data

(63) Continuation of application No. PCT/FR2006/002694, filed on Dec. 11, 2006.

(30) Foreign Application Priority Data

Dec. 12, 2005 (FR) .................... 05 12713

(51) Int. Cl.
*A61K 31/4196* (2006.01)
*C07D 249/08* (2006.01)

(52) U.S. Cl. ............... 514/383; 548/262.2; 548/267.2; 548/267.6

(58) Field of Classification Search ............. 548/262.2, 548/267.2, 267.6; 514/383
See application file for complete search history.

(56) References Cited

FOREIGN PATENT DOCUMENTS

WO WO 2004/026301 4/2004
WO WO 2006/074445 7/2006

OTHER PUBLICATIONS

Browne, E. J., et al., Triazoles. Part VI. 1,5-Diary1-1,2,4-Triazole-3-Aldehydes, Journal of the Chemical Society, pp. 575-583, (1962).
Dyck, B., et. al., Potent Imidazole and Triazole CB1 Receptor Antagonists Related to SR141716, Bioorganic & Medicinal Chemistry Letters, vol. 14, (2004), pp. 1151-1154.
Jagerovic, N., et. al., Discovery of 5-(4-Chlorophenyl)-1-(2,4-Dichlorophenyl)-3-Hexyl-1H-1,2,4-Triazole, a Novel in Vivo Cannabinoid Antagonist Containing a 1,2,4-Triazole Motif, J. Med. Chem. (2004), vol. 47, pp. 2939-2942.
Lange, J. H. M., et. al., Bioisosteric Replacements of the Pyrazole Moiety of Rimonabant: Synthesis, Biological Properties, and Molecular Modeling Investigation of Thiazoles, Triazoles, and Imidazoles as Potent and Selective CB1 Cannabinoid Receptor Antagonists, J. Med. Chem. (2005), vol. 48, pp. 1823-1838.

*Primary Examiner*—Golam M Shameem
(74) *Attorney, Agent, or Firm*—Balaram Gupta

(57) ABSTRACT

The invention concerns compounds of formula (I):

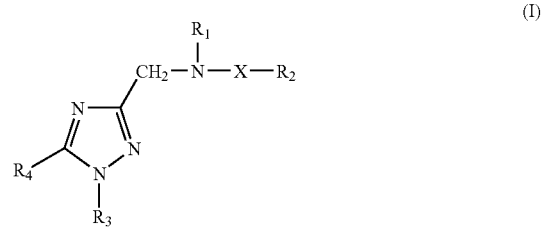

Wherein X, $R_1$, $R_2$, $R_3$ and $R_4$ are as described herein. The invention also concerns a method for preparing same and the therapeutic use thereof.

11 Claims, No Drawings

DIARYL TRIAZOLMETHYLAMINE DERIVATIVES, PREPARATION AND THERAPEUTIC USE THEREOF

This application is a continuation of International application No. PCT/FR2006/002,694, filed Dec. 11, 2006, which is incorporated herein by reference in its entirety; which claims the benefit of priority of French Patent Application No. 05/12,713, filed Dec. 12, 2005.

The present invention relates to diaryltriazolmethylamine derivatives, to their preparation and to their therapeutic use.

1,5-Diaryl-1,2,4-triazole-3-carboxamide derivatives are described as modulators of cannabinoid receptors in patent application WO 2004/026 301 and in Bioorg. Med. Chem. Lett., 2004, 14, p. 1151.

Patent application WO 2006/074 445 describes various heterocyclic compounds, especially triazole derivatives, as having activity on the cannabinoid $CB_1$ and $CB_2$ receptors.

Novel diaryltriazolmethylamine derivatives that have antagonist properties on the cannabinoid CB1 receptors have now been found.

One subject of the present invention is compounds corresponding to the formula:

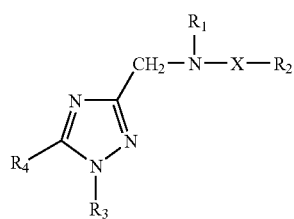

(I)

in which:

X represents a group

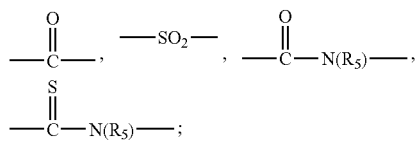

$R_1$ represents a hydrogen atom or a $(C_1-C_4)$alkyl group;

$R_2$ represents:

- a $(C_1-C_7)$alkyl, which is unsubstituted or substituted with a trifluoromethyl group or with a group $CO_2R_6$ or $CONR_7R_8$;
- a $C_3-C_{12}$ non-aromatic carbocyclic radical, which is unsubstituted or substituted one or more times with a $(C_1-C_4)$alkyl;
- a methyl substituted with a $C_3-C_{12}$ non-aromatic carbocyclic radical that is unsubstituted or substituted one or more times on the carbocycle with a $(C_1-C_4)$alkyl;
- a phenyl, which is unsubstituted or substituted one or more times with substituents independently chosen from a halogen atom, a $(C_1-C_4)$alkyl, a hydroxyl, a $(C_1-C_4)$alkoxy, a cyano, a trifluoromethyl group, a trifluoromethoxy group, a group $CO_2R_6$ or $CONR_7R_8$; or from a phenyl, phenoxy, pyrrolyl, imidazolyl, pyridyl or pyrazolyl radical, the said radicals being unsubstituted or substituted one or more times with a $(C_1-C_4)$alkyl;
- a phenoxymethyl, which is unsubstituted on the methyl or substituted on the methyl with one or two $(C_1-C_4)$alkyl groups, and unsubstituted on the phenyl or substituted on the phenyl with one or more substituents independently chosen from a halogen atom, a $(C_1-C_4)$alkyl, a $(C_1-C_4)$alkoxy, a trifluoromethyl group, a trifluoromethoxy group and a group $CO_2R_6$ or $CONR_7R_8$;
- a benzyl, which is unsubstituted or substituted one or more times on the phenyl with substituents independently chosen from a halogen atom, a cyano, a $(C_1-C_4)$alkyl, a $(C_1-C_4)$alkoxy, a trifluoromethyl group, a trifluoromethoxy group and a group $CO_2R_6$ or $CONR_7R_8$; or α-substituted with one or two identical or different groups chosen from a $(C_1-C_4)$alkyl and a $(C_3-C_7)$cycloalkyl;
- a benzhydryl or a benzhydrylmethyl group;
- a 1,2,3,4-tetrahydronaphthyl, which is unsubstituted or substituted one or more times with a $(C_1-C_4)$alkyl;
- a pyrrolyl, imidazolyl, pyridyl, pyrazolyl, furyl or thienyl radical, the said radicals being unsubstituted or substituted with one or more substituents independently chosen from a halogen atom, a $(C_1-C_4)$alkyl and a trifluoromethyl group;
- an indolyl, which is unsubstituted or substituted one or more times with substituents independently chosen from a halogen atom and a $(C_1-C_4)$alkyl;
- a benzofuryl, which is unsubstituted or substituted one or more times with substituents independently chosen from a halogen atom and a $(C_1-C_4)$alkyl;
- a 2,1,3-benzoxadiazolyl;

$R_3$ represents a phenyl, which is unsubstituted or substituted one or more times with substituents independently chosen from a halogen atom, a $(C_1-C_4)$alkyl, a $(C_1-C_4)$alkoxy, a trifluoromethyl or trifluoromethoxy group and a group $S(O)_n$Alk;

$R_4$ represents a phenyl, which is unsubstituted or substituted one or more times with substituents independently chosen from a halogen atom, a $(C_1-C_4)$alkyl, a $(C_1-C_4)$alkoxy, a trifluoromethyl or trifluoromethoxy group and a group $S(O)_n$Alk;

$R_5$ represents a hydrogen atom or a $(C_1-C_4)$alkyl;

$R_6$ represents a $C_1-C_4$ alkyl;

$R_7$ and $R_8$ represent each independently a hydrogen atom or a $(C_1-C_4)$alkyl;

n represents 0, 1 or 2;

Alk represents a $(C_1-C_4)$alkyl;

on condition that when X represents a group —CO— or —CONR_5—, $R_2$ is other than:

- a $C_4-C_7$ non-aromatic carbocyclic radical, which is unsubstituted or substituted one or more times with a $(C_1-C_4)$alkyl;
- a phenyl, which is unsubstituted or substituted one or more times with substituents independently chosen from a halogen atom, a $(C_1-C_4)$alkyl, a hydroxyl, a $(C_1-C_4)$alkoxy, a cyano, a trifluoromethyl group and a group $CO_2R_6$ or $CONR_7R_8$; or from a 1-pyrrolyl or 1-pyrazoyl radical, the said radicals being unsubstituted or substituted one or more times with a $(C_1-C_4)$alkyl;
- a 1,2,3,4-tetrahydronaphthalenyl, which is unsubstituted or substituted one or more times with a $(C_1-C_4)$alkyl;

a pyrrolyl, imidazolyl, pyridyl, pyrazolyl, furyl or thienyl radical, the said radicals being unsubstituted or substituted with one or more substituents independently chosen from a halogen atom, a $(C_1-C_4)$alkyl and a trifluoromethyl group;

an indolyl, which is unsubstituted or substituted one more times with substituents independently chosen from a halogen atom and a $(C_1-C_4)$alkyl;

a benzofuryl, which is unsubstituted or substituted one or more times with substituents independently chosen from a halogen atom and a $(C_1-C_4)$alkyl;

a 2,1,3-benzoxadiazolyl.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of hydrates or solvates, i.e. in the form of associations or combinations with one or more water molecules or with a solvent. Such hydrates and solvates also form part of the invention.

The term "halogen atom" means a bromine, chlorine, fluorine or iodine atom.

The terms "$(C_1-C_4)$alkyl" and "$(C_1-C_7)$alkyl" mean, respectively, a linear or branched alkyl radical of 1 to 4 carbon atoms or, respectively, of 1 to 7 carbon atoms, such as a methyl, ethyl, propyl, isopropyl, butyl, isobutyl, sec-butyl, tert-butyl, pentyl, isopentyl, hexyl, isohexyl or heptyl radical.

The term "$(C_1-C_4)$alkoxy" means a linear or branched alkoxy radical of 1 to 4 carbon atoms such as a methoxy, ethoxy, propoxy, isopropoxy, butoxy, sec-butoxy or tert-butoxy radical.

The term "$(C_3-C_{12})$ non-aromatic carbocyclic radical" means: a monocyclic radical or a fused or bridged bicyclic or tricyclic radical; the term "monocyclic radical" means a cycloalkyl, for example cyclopropyl, cyclobutyl, cyclopentyl, cyclohexyl or cycloheptyl, the cyclopentyl, cyclohexyl and cycloheptyl radicals being preferred; the term "fused or bridged bicyclic or tricyclic radical" means, for example, bicyclo[2.2.1]heptyl, bicyclo[2.2.2]octyl, bicyclo[3.2.1]octyl or adamantyl.

Among the compounds of formula (I) that are subjects of the invention, mention is made of:

the compounds of formula (IA) in which —X— represents a group —CO— and the substituents $R_1$ to $R_4$ are as defined for the compounds of formula (I);

the compounds of formula (IB) in which —X— represents a group —SO$_2$— and the substituents $R_1$ to $R_4$ are as defined for the compounds of formula (I);

the compounds of formula (IC) in which —X— represents a group —CON(R$_5$)— and the substituents $R_1$ to $R_5$ are as defined for the compounds of formula (I);

the compounds of formula (ID) in which —X— represents a group —CSN(R$_5$)— and the substituents $R_1$ to $R_5$ are as defined for the compounds of formula (I).

Among the compounds that are subjects of the invention, the compounds that are preferred are those of formula (I) in which:

$R_1$ represents a hydrogen atom;

$R_2$ has one of the values defined for (I);

$R_3$ and $R_4$ represent a 2,4-dichlorophenyl and a 4-chlorophenyl, a 4-chlorophenyl and a 2,4-dichlorophenyl, or a 2,4-dichlorophenyl and a 4-methoxyphenyl;

and also the hydrates or solvates thereof.

The compounds that are most particularly preferred are those of formula (I) in which the substituents $R_1$, $R_3$ and $R_4$ are as defined above and $R_2$ represents a benzhydrylmethyl or benzhydryl group;

and also the hydrates or solvates thereof.

Compounds that are also preferred are those of formulae (IB) and (ID) in which the substituents $R_1$, $R_3$ and $R_4$ are as defined above and $R_2$ represents a group chosen from:

a phenyl substituted one or more times with substituents independently chosen from a halogen atom, a $(C_1-C_4)$ alkyl, a trifluoromethyl group and a trifluoromethoxy group;

a benzhydrylmethyl or benzhydryl group;

a 2-indolyl radical, which is unsubstituted or substituted with a $(C_1-C_4)$alkyl;

and also the hydrates or solvates thereof.

In accordance with the invention, the compounds of formula (I) may be prepared according to a process that is characterized in that:

a compound of formula:

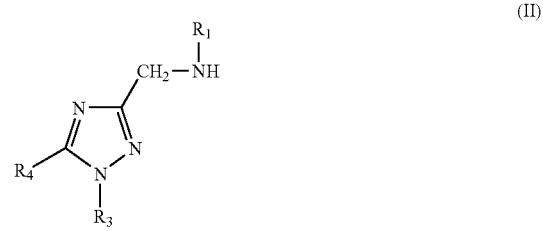

(II)

in which $R_1$, $R_3$ and $R_4$ are as defined for a compound of formula (I) is treated:

either with an acid or a functional derivative of this acid of formula:

HOOC—R$_2$ (III)

in which $R_2$ is as defined for a compound of formula (I), when a compound of formula (IA) needs to be prepared, in which —X— represents a group —CO—;

or with a sulfonyl halide of formula:

Hal-SO$_2$—R$_2$ (IV)

in which $R_2$ is as defined for a compound of formula (I) and Hal represents a halogen atom, preferably chlorine, when a compound of formula (IB) needs to be prepared, in which —X— represents a group —SO$_2$—;

or with a haloformate of formula:

HalCOOAr (V)

in which Hal represents a halogen atom and Ar represents a phenyl or a 4-nitrophenyl, to obtain an intermediate compound of formula:

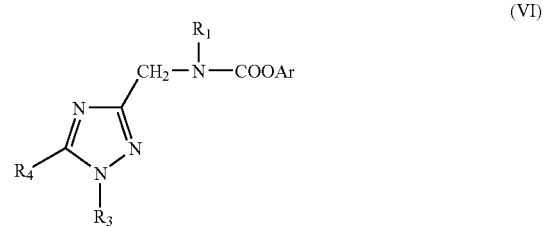

(VI)

in which $R_1$, $R_3$ and $R_4$ are as defined for a compound of formula (I), which is then reacted with an amine of formula:

$$HN(R_5)R_2 \quad (VII)$$

in which $R_2$ and $R_5$ are as defined for a compound of formula (I), when a compound of formula (IC) needs to be prepared, in which —X— represents a group —$CON(R_5)$—;

or with an isothiocyanate $R_2N=C=S$ (VIII), when a compound of formula (ID) needs to be prepared, in which —X— represents a group —CSNH—.

Where appropriate, a compound of formula (IC) or (ID) in which $R_5$ represents a $(C_1-C_4)$alkyl group may be prepared via an alkylation reaction on the corresponding compound of formula (I) in which $R_5$ represents a hydrogen atom.

Optionally, the compound of formula (I) is converted into an acid-addition salt thereof.

When a compound of formula (II) is treated with the acid of formula (III) itself, the process is performed in the presence of a coupling agent used in peptide chemistry, such as 1,3-dicyclohexylcarbodiimide (DCC) or benzotriazol-1-yloxy-tris(dimethylamino)phosphonium (BOP) hexafluorophosphate or benzotriazol-1-yloxytris(pyrrolidino)phosphonium (PyBOP) hexafluorophosphate or 2-(1H-benzotriazol-1-yl)-1,1,3,3-tetramethyluronium tetrafluoroborate (TBTU), in the presence of a base such as triethylamine, N,N-diisopropylethylamine or 4-dimethylaminopyridine, in a solvent such as dichloromethane, dichloroethane, N,N-dimethylformamide or tetrahydrofuran, at a temperature of between $-10°$ C. and the reflux temperature of the solvent.

As functional derivative of the acid (III), it is possible to use the acid chloride, the anhydride, a mixed anhydride, a $C_1-C_4$ alkyl ester in which the alkyl is straight or branched, and an activated ester, for example p-nitrophenyl ester.

Thus, in the process according to the invention, the acid chloride obtained by reacting thionyl chloride or oxalyl chloride with the acid of formula (III) can also be reacted with the compound of formula (II), in a solvent, such as a chlorinated solvent (for example dichloromethane, dichloroethane or chloroform), an ether (for example tetrahydrofuran or dioxane) or an amide (for example N,N-dimethylformamide), under an inert atmosphere, at a temperature of between 0° C. and room temperature, in the presence of a tertiary amine such as triethylamine, N-methylmorpholine or pyridine.

One variant consists in preparing the mixed anhydride of the acid of formula (III) by reacting ethyl chloroformate with the acid of formula (III), in the presence of a base such as triethylamine, and in reacting it with the compound of formula (II), in a solvent such as dichloromethane, under an inert atmosphere, at room temperature, in the presence of a base such as triethylamine.

When a compound of formula (II) is treated with a sulfonyl halide of formula (IV), the process is performed in the presence of a base such as triethylamine or diisopropylethylamine, in a solvent such as dichloromethane or tetrahydrofuran and at a temperature of between room temperature and the reflux temperature of the solvent.

When a compound of formula (II) is treated with a haloformate of formula (V), the process is performed in the presence of a base such as triethylamine, in a solvent such as dichloromethane and at a temperature of between 0° C. and room temperature. The intermediate compound of formula (VI) thus obtained is then reacted with an amine of formula (VII), in a solvent such as dichloromethane, in the presence of a base such as triethylamine and at a temperature of between 0° C. and the reflux temperature of the solvent.

According to one variant of the process, the compounds of formula (IC) in which —X— represents a group —CON($R_5$)— in which $R_5$=H, may be prepared by reacting a compound of formula (II) with an isocyanate of formula $R_2—N=C=O$ (VIII), in the presence of a base such as triethylamine, in a solvent such as dichloromethane and at a temperature of between room temperature and the reflux temperature of the solvent.

According to another variant of the process, the compounds of formula (IC) in which —X— represents a group —$CON(R_5)$— may be prepared by reacting a compound of formula (II) with a compound of formula $ClCON(R_5)R_2$ (IX) in the presence of a base such as triethylamine, in a solvent such as dichloromethane and at a temperature of between 0° C. and room temperature.

The compounds of formula (IA), (IB), (IC with $R_5 \neq H$), (ID with $R_5 \neq H$) in which $R_1$ represents a $(C_1-C_4)$alkyl may also be prepared from the corresponding compounds of formula (I) in which $R_1$ represents a hydrogen atom, via a method chosen from the methods known to those skilled in the art, such as alkylation with an alkyl halide.

The compounds of formula (I) thus obtained may be subsequently separated from the reaction medium and purified according to the standard methods, for example by crystallization or chromatography.

The compounds of formula (II) may be prepared according to the following reaction scheme:

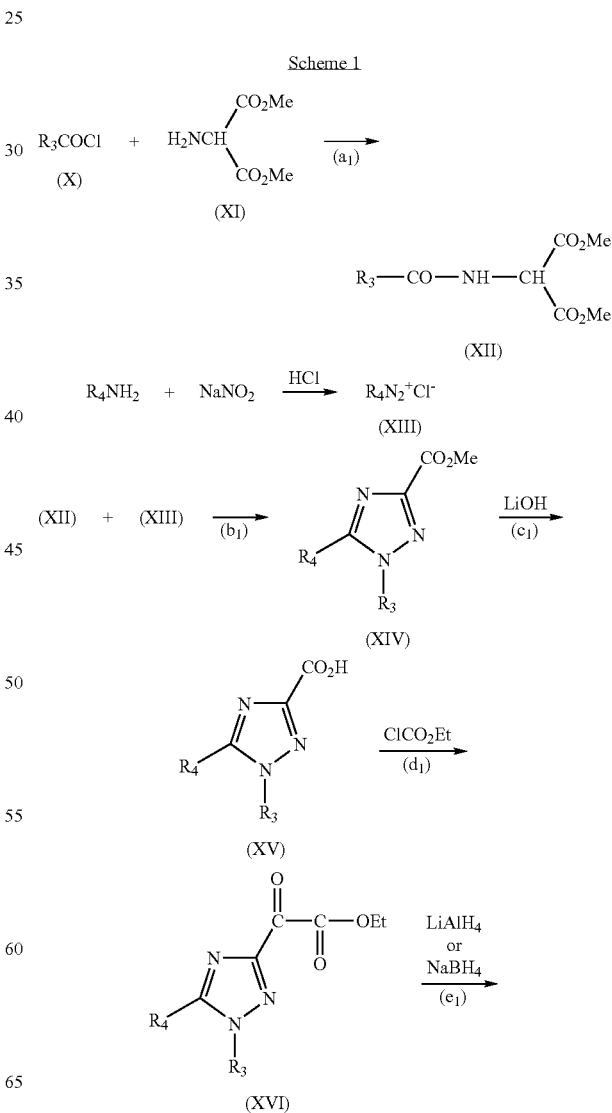

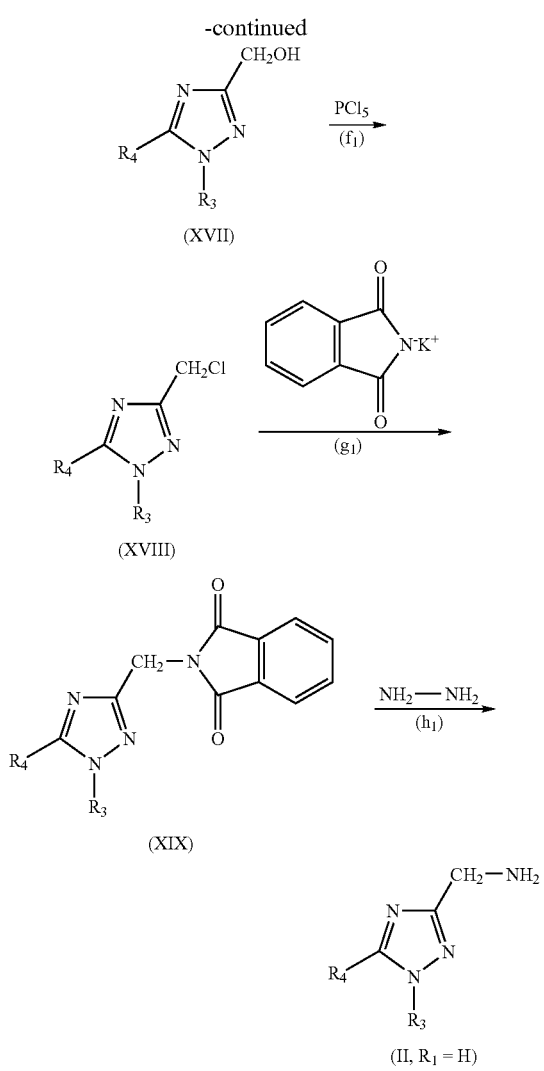

In step $a_1$, the malonate of formula (XII) is prepared by the action of the acid chloride $R_3COCl$ (X) on the dimethylamino malonate (XI). The diazonium chloride of formula (XIII) is then prepared, which is reacted with the malonate of formula (XII) to obtain in step $b_1$ the ester derivative of 1,5-diphenyl-1H-1,2,4-triazole-3-carboxylic acid. In step $b_1$, the ester is hydrolyzed, for example with LiOH, and in step $d_1$, ethyl chloroformate is then reacted to prepare the compound of formula (XVI). This compound is reduced in step $c_1$, for example with a reducing agent such as $LiAlH_4$ or $NaBH_4$ and the alcohol of formula (XVII) obtained is treated with a chlorinating agent such as $PCl_5$. Potassium phthalimide is then reacted (step $g_1$), followed by hydrazine hydrate (step $h_1$) to prepare the compound of formula (II).

Where appropriate, a compound of formula (II) in which $R_1$ represents a hydrogen atom may be converted to a compound of formula (II) in which $R_1$ is a $(C_1-C_4)$allyl by using methods known to those skilled in the art, for instance reaction with an alkylating agent, reductive amination with an aldehyde in reductive medium, or acylation with an acid chloride followed by reduction.

Preferentially, the oxazoles of formula (II) are prepared according to the following reaction scheme:

The examples that follow describe the preparation of certain compounds in accordance with the invention. The examples are not limiting, and serve merely to illustrate the present invention. In the Preparations and the Examples, the following abbreviations are used:
DMF: N,N-dimethylformamide
THF: tetrahydrofuran
DCM: dichloromethane
MeOH: methanol
TFA: trifluoroacetic acid
AcOH: acetic acid
DBU: 1,8-diazabicyclo[5.4.0]undec-7-ene
DCC: 1,3-dicyclohexylcarbodiimide
DIPEA: diisopropylethylamine
BOP: benzotriazol-1-yloxytris(dimethylamino)phosphonium hexafluorophosphate
PyBOP: benzotriazol-1-yloxytris(pyrrolidino)phosphonium hexafluorophosphate
TBTU: 2-(1H-benzotriazol-1-yl)-1,1,3,3-tetramethyluronium tetrafluoroborate
Yld: yield
rt: room temperature
HPLC: high-performance liquid chromatography.

The compounds according to the invention are analyzed by LC/UV/MS coupling (liquid chromatography/UV detection/mass spectrometry). The molecular peaks ($MH^+$) and the retention time (t) in minutes are measured.

Conditions MS2
An XTerra MS C18 column of 2.1×30 mm, 3.5 μm is used, at 30° C., flow rate 0.8 ml/minute.
The eluent is composed as follows:
solvent A: 0.025% trifluoroacetic acid (TFA) in water;
solvent B: 0.025% TFA in acetonitrile.
Gradient:

| Time (min) | % A | % B |
|---|---|---|
| 0 | 100 | 0 |
| 2 | 0 | 100 |
| 2.7 | 0 | 100 |
| 2.75 | 100 | 0 |

The UV detection is performed with a diode array detector between 210 and 400 nm and the mass detection is performed in positive ESI chemical ionization mode.

Conditions MS5
An XTerra MS C18 column of 2.1×30 mm, 3.5 μm is used, flow rate 1 ml/minute.
The eluent is composed as follows:
Solvent A: 0.025% TFA in water,
Solvent B: 0.025% TFA in acetonitrile.
Gradient:

| Time (min) | % A | % B |
|---|---|---|
| 0 | 100 | 0 |
| 2 | 0 | 100 |
| 2.7 | 0 | 100 |
| 2.75 | 100 | 0 |

The UV detection is performed with a diode array detector between 210 and 400 nm and the mass detection is performed in positive ESI mode.

Method A:

A Symmetry C18 column of 2.1×50 mm, 3.5 μm is used, at 30° C., flow rate 0.4 ml/minute.

The eluent is composed as follows:

Solvent A: 0.005% trifluoroacetic acid (TFA) in water at pH 3.15;

Solvent B: 0.005% TFA in acetonitrile.

Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

The UV detection is performed at λ 220 nm and the mass detection is performed in positive ESI chemical ionization mode.

Preparations

1. Preparation of the Compounds of Formula (II)

Preparation 1.1

1-(1-(4-Chlorophenyl)-5-(2,4-dichlorophenyl)-1H-1,2,4-triazol-3-yl)methanamine

A) Dimethyl((2,4-dichlorobenzoyl)amino)malonate

To a solution of 5 g of the dimethylamino malonate in DCM (60 ml) are added 13.2 ml of triethylamine. After stirring for 30 minutes at room temperature, 5.2 g of the 2,4-dichlorobenzoyl are added slowly to the reaction medium. The mixture is stirred at room temperature for two hours. The medium is then diluted with DCM (50 ml) and successively washed with aqueous HCl solution (3N), and then with water. The organic phase is dried over $Na_2SO_4$, filtered and evaporated to dryness to give the expected crude product (yield=90%).

B) Methyl 1-(4-chlorophenyl)-5-(2,4-dichlorophenyl)-1H-1,2,4-triazole-3-carboxylate To a solution prepared beforehand containing 3.25 g of 4-chloroaniline, 15 ml of acetic acid and 5 ml of concentrated HCl are added slowly, with cooling, 1.9 g of $NaNO_2$ dissolved in 15 ml of water. The reaction medium is stirred for 30 minutes. This heterogeneous solution is added slowly, with cooling, to a mixture prepared beforehand containing 7.4 g of the compound prepared in the preceding step and 6.3 g of sodium acetate in 40 ml of methanol. The mixture is stirred at room temperature for two hours. The heterogeneous medium is filtered. The filtrate is evaporated to dryness and a methanol-water mixture is added. The new precipitate formed is recovered by filtration. The combined precipitates are placed in 50 ml of methanol and treated with a solution of MeONa/MeOH (150 mg of Na in 20 ml of MeOH). The mixture is stirred at room temperature for one hour and evaporated to dryness. The crude product obtained is used directly in the following step.

C) 1-(4-Chlorophenyl)-5-(2,4-dichlorophenyl)-1H-1,2,4-triazole-3-carboxylic acid The crude reaction product obtained in the preceding step is placed in a THF—$H_2O$ mixture (155 ml/55 ml), and 1.15 g of LiOH diluted in a minimum amount of water are then added at 0° C. After stirring for one hour at 0° C., the reaction medium is washed with ether. The aqueous phase is acidified (~pH 1) with $KHSO_4$ solution. The mixture is extracted with ethyl acetate. The organic phase is dried over $Na_2SO_4$, filtered and evaporated to dryness to give the expected compound (yield=79%).

D) (1-(4-Chlorophenyl)-5-(2,4-dichlorophenyl)-1H-1,2,4-triazol-3-yl)methanol

To a solution of 6.7 g of the acid derivative obtained in the preceding step in THF (4.5 ml) are added at 0° C. 3 ml of $Et_3N$ followed by 1.9 ml of ethyl chloroformate. After stirring for 15 minutes at 0° C., 2.0 g of $NaBH_4$ are added. Methanol is then added dropwise. After stirring for 30 minutes at 0° C., the mixture is hydrolyzed by addition of aqueous HCl solution (1N). The mixture is evaporated to dryness and then taken up in THF (120 ml) and 0.8 g of $LiAlH_4$ is added portionwise every 30 minutes. The mixture is hydrolyzed in a conventional manner and filtered through silica to give the expected compound (yield=63%).

E) 3-(Chloromethyl)-1-(4-chlorophenyl)-5-(2,4-dichlorophenyl)-1H-1,2,4-triazole

To a solution of 4 g of the alcohol derivative prepared in the preceding step in 75 ml of DCM are added portionwise at 0° C. 4.7 g of $PCl_5$. The mixture is stirred at room temperature for 4 hours 30 minutes. The reaction medium is poured into a water-ice mixture. The resulting mixture is extracted with DCM. The organic phase is washed with saturated NaIl solution. The organic phase is dried over $Na_2SO_4$, filtered and evaporated to dryness to give the expected product (yield=97%).

F) 2-((1-(4-Chlorophenyl)-5-(2,4-dichlorophenyl)-1H-1,2,4-triazol-3-yl)methyl)-1H-isoindole-1,3-(2H)-dione To a solution of 4.1 g of the chloro derivative obtained in the preceding step in DMF (30 ml) are added 1.6 g of NaI followed by 2.2 g of potassium 1,3-dioxo-1,3-dihydroisoindol-2-ide. The mixture is heated at 65° C. for 3 hours. The reaction medium is cooled to room temperature. The medium is diluted with ethyl acetate and successively washed with aqueous NaOH solution (0.2N) and then with water. The heterogeneous mixture is filtered. The organic phase is dried over $Na_2SO_4$, filtered and evaporated to dryness. The expected product is present in the precipitate and in the evaporated filtrate in a total yield of 87%.

G) 1-(1-(4-Chlorophenyl)-5-(2,4-dichlorophenyl)-1H-1,2,4-triazol-3-yl)-methanamine To a solution of 2.2 g of the phthalimide derivative obtained in the preceding step in 30 ml of ethanol are added 1.9 ml of hydrazine hydrate. The mixture is heated at the reflux temperature of the solvent for one hour. The heterogeneous medium is cooled to room temperature and filtered. The precipitate is rinsed with ethanol. The filtrate is evaporated to dryness, taken up in ethyl acetate and then washed several times with aqueous NaOH solution (0.2N). The organic phase is dried over $Na_2SO_4$, filtered and evaporated to dryness. The expected product is isolated by formation of its hydrochloride in ethyl ether-HCl (yield=70%).

Other intermediates of formula (II) with Y=O were prepared according to the procedure described below.

TABLE I (II, $R_1$ = H)

| Preparation No | R3 | R4 | Characterization (conditions) |
|---|---|---|---|
| Preparation 1.1 | 4-Cl-phenyl | 2,5-diCl-phenyl | $MH^+$ = 352.9<br>t = 6.56<br>(A) |
| Preparation 1.2 | 2,4-diCl-phenyl | 4-Cl-phenyl | $MH^+$ = 352.9<br>t = 6.55<br>(A) |
| Preparation 1.3 | 2,4-diCl-phenyl | 4-OMe-phenyl | $MH^+$ = 348.9<br>t = 6.16<br>(A) |

EXAMPLE 1

The compounds of formula (I) in which —X—=—CO— are prepared by combinatorial chemistry according to the process described below:

The carboxylic acids of formula (III) are dissolved in DMF to a concentration of 0.25 M in the presence of 3 equivalents of DIPEA. 120 µl of these solutions are placed in each 2 ml well and 120 µl of a solution of TBTU in DMF at a concentration of 0.25 M are added. 300 µl of a solution containing the methylamine of formula (II) in DMF at a concentration of 0.1 M and 3 equivalents of DIPEA are added to each well. The plates are shaken at rt for 16 hours and then evaporated. The products formed in each well are dissolved in 500 µl of EtOAc, 400 µl of 0.1 M $Na_2CO_3$ are then added and the plates are shaken. After separation of the phases by settling, 430 µl of aqueous phase are discarded, 300 µl of 5% NaCl are then added and the plates are shaken. 350 µl of aqueous phase are then discarded by LC/UV/MS and the rest is evaporated under vacuum to obtain the expected compounds.

EXAMPLE 2

The compounds of formula (I) in which —X—=—CONH— are prepared by combinatorial chemistry according to the process described below:

The compounds of formula (II) are dissolved in DMF to a concentration of 0.1 M in the presence of 3 equivalents of DIPEA. 300 µl of these solutions are placed in each 2 ml well and 120 µl of a solution containing the isocyanate compound of formula (VIII) in THF at a concentration of 0.25 M are added. The plates are shaken at rt for 16 hours. The products formed in each well are dissolved by adding 500 µl of EtOAc, 400 µl of 0.1 M $Na_2CO_3$ are added, and the plates are shaken. After separation of the phases by settling, 430 µl of aqueous phase are discarded, 300 µl of 5% NaCl are added and the plates are shaken. After separation of the phases by settling, 350 µl of aqueous phase are discarded, 20 µl are taken for analysis by LC/UV/MS and the rest is evaporated under vacuum to obtain the expected compounds.

EXAMPLE 3

The compounds of formula (I) in which —X—=—$SO_2$— are prepared by combinatorial chemistry according to the process described below:

The compounds of formula (II) are dissolved in DMF to a concentration of 0.1 M in the presence of 3 equivalents of DIPEA. 300 µl of these solutions are added to each 2 ml well and 120 µl of a solution containing the corresponding sulfonyl chloride of formula (IV) in THF at a concentration of 0.25 M are added. The plates are shaken at rt for 16 hours and then evaporated. The products formed in each well are dissolved by adding 500 µl of EtOAc, 400 µl of 0.1 M $Na_2CO_3$ are added and the plates are shaken. After separation of the phases by settling, 430 µl of aqueous phase are discarded, 300 µl of 5% NaCl are added and the plates are shaken. After separation of the phases by settling, 350 µl of aqueous phase are discarded, 20 µl of taken for analysis by LC/UV/MS and the rest is evaporated under vacuum to obtain the expected compounds.

The tables that follow illustrate the chemical structures and the physical properties of a number of compounds according to the invention. In these tables, Me, Et, nPr and tBu illustrate, respectively, methyl, ethyl, n-propyl and tert-butyl groups.

TABLE III (I)

Structure: triazole with CH₂—NH—X—R₂ substituent, R4, R3 groups

| Compound No. | R₂ | X | R₃ | R₄ | Characterization Conditions |
|---|---|---|---|---|---|
| 1 | —CH(phenyl)(phenyl) | —CONH— | 2,4-dichlorophenyl | 4-chlorophenyl | MH⁺ = 562.5<br>t = 1.92<br>MS 2 |
| 2 | 4-(OCF₃)phenyl | —CO— | 2,4-dichlorophenyl | 4-chlorophenyl | MH⁺ = 541.4<br>t = 1.93<br>MS 2 |
| 3 | —CH₂—CH(phenyl)(phenyl) | —CO— | 2,4-dichlorophenyl | 4-chlorophenyl | MH⁺ = 561.5<br>t = 1.95<br>MS 2 |
| 4 | 4-(OCF₃)phenyl | —CO— | 4-chlorophenyl | 2,4-dichlorophenyl | MH⁺ = 540.8<br>t = 2.38<br>MS 5 |
| 5 | 4-(CF₃)phenyl | —C(S)NH— | 4-chlorophenyl | 2,4-dichlorophenyl | MH⁺ = 555.8<br>t = 2.00<br>MS 5 |
| 6 | —CH₂—CH(phenyl)(phenyl) | —CO— | 2,4-dichlorophenyl | 4-methoxyphenyl | MH⁺ = 557.6<br>t = 1.86<br>MS 2 |

TABLE III-continued (I)

Structure: triazole with CH₂—NH—X—R₂ substituent, R4 and R3 groups

| Compound No. | R₂ | X | R₃ | R₄ | Characterization Conditions |
|---|---|---|---|---|---|
| 7 | 3-methyl-5-methyl-2-trifluoromethyl furan | —SO₂— | 2,4-dichlorophenyl | 4-methoxyphenyl | MH⁺ = 560.8<br>t = 2.31<br>MS 5 |
| 8 | 3-methylphenyl phenyl ether | —CO— | 4-chlorophenyl | 2,5-dichlorophenyl | MH⁺ = 548.8<br>t = 2.42<br>MS 5 |
| 9 | —CH(pyrrol-1-yl)(phenyl) | —CO— | 2,4-dichlorophenyl | 4-chlorophenyl | MH⁺ = 535.8<br>t = 2.35<br>MS 5 |
| 10 | 2-methylthiophene | —SO₂— | 2,4-dichlorophenyl | 4-chlorophenyl | MH⁺ = 499.4<br>t = 1.82<br>MS 2 |
| 11 | 4-phenoxyphenyl | —CO— | 4-chlorophenyl | 2,5-dichlorophenyl | MH⁺ = 548.8<br>t = 2.44<br>MS 5 |
| 12 | —CH(phenyl)(cyclohexyl) | —CO— | 2,4-dichlorophenyl | 4-chlorophenyl | MH⁺ = 553.6<br>t = 2.06<br>MS 2 |

TABLE III-continued (I)

Structure: 5-membered 1,2,4-triazole ring with substituents: position 3 bears CH₂—NH—X—R₂, position 5 bears R₄, position 1 (N) bears R₃.

| Compound No. | R₂ | X | R₃ | R₄ | Characterization Conditions |
|---|---|---|---|---|---|
| 13 | —(CH₂)₂—C(=O)—N(Me)Me | —CO— | 2,4-diClPh | 4-OMePh | MH⁺ = 476.6, t = 1.48, MS 2 |
| 14 | —CH(Ph)(Ph) | —CONH— | 2,4-diClPh | 4-OMePh | MH⁺ = 557.9, t = 2.27, MS 5 |
| 15 | —CH(nPr)(nPr) | —CO— | 2,4-diClPh | 4-ClPh | MH⁺ = 479.6, t = 1.94, MS 2 |
| 16 | 3-Cl-phenyl | —SO₂— | 2,4-diClPh | 4-OMePh | MH⁺ = 522.8, t = 2.25, MS 5 |
| 17 | 3,5-diMe-phenyl | —SO₂— | 2,4-diClPh | 4-ClPh | MH⁺ = 521.5, t = 1.93, MS 2 |
| 18 | —CH₂—(2-F-phenyl) | —CONH— | 2,4-diClPh | 4-OMePh | MH⁺ = 499.9, t = 2.13, MS 5 |

The compounds of formula (I) show very good in vitro affinity ($IC_{50} \leq 5 \times 10^{-7}$ M) for the $CB_1$ cannabinoid receptors, under the experimental conditions described by M. Rinaldi-Carmona et al. (FEBS Letters, 1994, 350, 240-244).

The antagonist nature of the compounds of formula (I) was demonstrated by means of the results obtained in models of inhibition of adenylate cyclase, as described in M. Bouaboula et al., J. Biol. Chem., 1995, 270, 13973-13980, M. Rinaldi-Carmona et al., J. Pharmacol. Exp. Ther., 1996, 278, 871-878 and M. Bouaboula et al., J. Biol. Chem., 1997, 272, 22330-22339.

The toxicity of the compounds of formula (I) is compatible with their use as medicaments.

Thus, according to another of its aspects, a subject of the invention is medicaments for human and veterinary medicine, comprising a compound of formula (I), or alternatively a solvate or a hydrate of the compound of formula (I).

Thus, the compounds according to the invention may be used in the treatment or prevention of diseases involving the $CB_1$ cannabinoid receptors in man or animals.

For example, and in a non-limiting manner, the compounds of formula (I) are useful as psychotropic medicaments, especially for treating psychiatric disorders including anxiety, depression, mood disorders, insomnia, delirium disorders, obsessive disorders, psychoses in general, schizophrenia, attention and hyperactivity disorders (AHD) in hyperkinetic children (MBD), and also for the treatment of disorders associated with the use of psychotropic substances, especially in the case of a substance abuse and/or dependency on a substance, including alcohol dependency and nicotine dependency.

The compounds of formula (I) according to the invention may be used as medicaments for treating migraine, stress, diseases of psychosomatic origin, panic attacks, epilepsy, motor disorders, in particular dyskinesia or Parkinson's disease, trembling and dystonia.

The compounds of formula (I) according to the invention may also be used as medicaments in the treatment of memory disorders, cognitive disorders, in particular in the treatment of senile dementia and Alzheimer's disease, and also in the treatment of attention or consciousness disorders. Furthermore, the compounds of formula (I) may be useful as neuroprotective agents, in the treatment of ischaemia, cranial trauma and the treatment of acute or chronic neurodegenerative diseases: including chorea, Huntington's chorea and Tourrette's syndrome.

The compounds of formula (I) according to the invention may be used as medicaments in the treatment of pain: neuropathic pain, acute peripheral pain, chronic pain of inflammatory origin.

The compounds of formula (I) according to the invention may be used as medicaments in human or veterinary medicine, in the treatment of appetite disorders, appetence disorders (for sugars, carbohydrates, drugs, alcohol or any appetizing substance) and/or eating behavioral disorders, especially for the treatment of obesity or bulimia and also for the treatment of type II diabetes or non-insulin-dependent diabetes and for the treatment of dyslipidemias and metabolic syndrome. Thus, the compounds of formula (I) according to the invention are useful in the treatment of obesity and the risks associated with obesity, especially the cardiovascular risks. Furthermore, the compounds of formula (I) according to the invention may be used as medicaments in the treatment of gastrointestinal disorders, diarrhea disorders, ulcers, vomiting, bladder and urinary disorders, disorders of endocrine origin, cardiovascular disorders, hypotension, hemorrhagic shock, septic shock, chronic liver cirrhosis, hepatic steatosis, steatohepatitis, asthma, Raynaud's syndrome, glaucoma, fertility disorders, premature interruption of pregnancy, premature birth, inflammatory phenomena, immune system diseases, in particular autoimmune diseases and neuroinflammatory diseases such as rheumatoid arthritis, rectional arthritis, diseases resulting in demyelinization, multiple sclerosis, infectious and viral diseases such as encephalitis, strokes, and also as medicaments for anticancer chemotherapy, for the treatment of Guillain-Barré syndrome and for the treatment of bone diseases and osteoporosis.

According to the present invention, the compounds of formula (I) are most particularly useful for treating psychotic disorders, in particular schizophrenia, attention and hyperactivity disorders (AHD) in hyperkinetic children; appetite and obesity disorders; memory and cognitive deficits; alcohol dependency, nicotine dependency, i.e. weaning from alcohol and weaning from tobacco.

More particularly, the compounds of formula (I) according to the present invention are useful in the treatment and prevention of appetite disorders, metabolic disorders, gastrointestinal disorders, inflammatory phenomena, immune system diseases, psychotic disorders, alcohol dependency and nicotine dependency.

According to one of its aspects, the present invention relates to the use of a compound of formula (I), and solvates or hydrates thereof for treating the disorders and diseases indicated above.

According to another of its aspects, the present invention relates to pharmaceutical compositions comprising, as active principle, a compound according to the invention. These pharmaceutical compositions contain an effective dose of at least one compound according to the invention, a solvate or a hydrate of the said compound, and also at least one pharmaceutically acceptable excipient.

The said excipients are chosen according to the pharmaceutical form and the desired mode of administration, from the usual excipients known to those skilled in the art.

In the pharmaceutical compositions of the present invention for oral, sublingual subcutaneous, intramuscular, intravenous, topical, local, intratracheal, intranasal, transdermal or rectal administration, the active principle of formula (I) above, or the possible solvate or hydrate thereof, may be administered in a unit form of administration, as a mixture with standard pharmaceutical excipients, to man and animals for the prophylaxis or treatment of the above disorders or diseases.

The appropriate unit forms of administration include oral-route forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application, the compounds according to the invention may be used in creams, gels, pomades or lotions.

By way of example, a unit form of administration of a compound according to the invention in tablet form may comprise the following components:

| | |
|---|---:|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

Via the oral route, the dose of active principle administered per day may be from 0.01 to 100 mg/kg in one or more dosage intakes, preferentially 0.02 to 50 mg/kg.

There may be particular cases in which higher or lower dosages are appropriate; such dosages do not depart from the context of the invention. According to the usual practice, the dosage that is appropriate to each patient is determined by the doctor according to the mode of administration and the weight and response of the said patient.

According to another of its aspects, the present invention also relates to a method for treating the pathologies indicated above, which comprises the administration to a patient of an effective dose of a compound according to the invention, or a hydrate or solvate.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of formula (I):

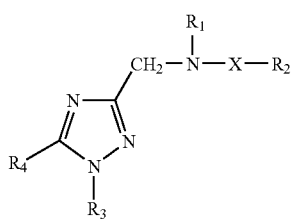

wherein:

X represents a group

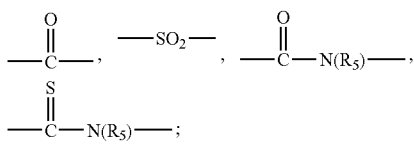

$R_1$ represents a hydrogen atom or a $(C_1-C_4)$alkyl group;

$R_2$ represents:
- a $(C_1-C_7)$alkyl, which is unsubstituted or substituted with a trifluoromethyl group or with a group $CO_2R_6$ or $CONR_7R_8$;
- a $C_3-C_{12}$ non-aromatic carbocyclic radical, which is unsubstituted or substituted one or more times with a $(C_1-C_4)$alkyl;
- a methyl substituted with a $C_3-C_{12}$ non-aromatic carbocyclic radical that is unsubstituted or substituted one or more times on the carbocycle with a $(C_1-C_4)$alkyl;
- a phenyl, which is unsubstituted or substituted one or more times with substituents independently chosen from a halogen atom, a $(C_1-C_4)$alkyl, a hydroxyl, a $(C_1-C_4)$alkoxy, a cyano, a trifluoromethyl group, a trifluoromethoxy group, a group $CO_2R_6$ or $CONR_7R_8$; or from a phenyl, phenoxy, pyrrolyl, imidazolyl, pyridyl or pyrazolyl radical, said radicals being unsubstituted or substituted one or more times with a $(C_1-C_4)$alkyl;
- a phenoxymethyl, which is unsubstituted on the methyl or substituted on the methyl with one or two $(C_1-C_4)$alkyl groups, and unsubstituted on the phenyl or substituted on the phenyl with one or more substituents independently chosen from a halogen atom, a $(C_1-C_4)$alkyl, a $(C_1-C_4)$alkoxy, a trifluoromethyl group, a trifluoromethoxy group and a group $CO_2R_6$ or $CONR_7R_8$;
- a benzyl, which is unsubstituted or substituted one or more times on the phenyl with substituents independently chosen from a halogen atom, a cyano, a $(C_1-C_4)$alkyl, a $(C_1-C_4)$alkoxy, a trifluoromethyl group, a trifluoromethoxy group and a group $CO_2R_6$ or $CONR_7R_8$; or α-substituted with one or two identical or different groups chosen from a $(C_1-C_4)$alkyl and a $(C_3-C_7)$cycloalkyl;
- a benzhydryl or a benzhydrylmethyl group;
- a 1,2,3,4-tetrahydronaphthyl, which is unsubstituted or substituted one or more times with a $(C_1-C_4)$alkyl;
- a pyrrolyl, imidazolyl, pyridyl, pyrazolyl, furyl or thienyl radical, the said radicals being unsubstituted or substituted with one or more substituents independently chosen from a halogen atom, a $(C_1-C_4)$alkyl and a trifluoromethyl group;
- an indolyl, which is unsubstituted or substituted one or more times with substituents independently chosen from a halogen atom and a $(C_1-C_4)$alkyl;
- a benzofuryl, which is unsubstituted or substituted one or more times with substituents independently chosen from a halogen atom and a $(C_1-C_4)$alkyl; and
- a 2,1,3-benzoxadiazolyl;

$R_3$ represents a phenyl, which is unsubstituted or substituted one or more times with substituents independently chosen from a halogen atom, a $(C_1-C_4)$alkyl, a $(C_1-C_4)$alkoxy, a trifluoromethyl or trifluoromethoxy group and a group $S(O)_n$Alk;

$R_4$ represents a phenyl, which is unsubstituted or substituted one or more times with substituents independently chosen from a halogen atom, a $(C_1-C_4)$alkyl, a $(C_1-C_4)$alkoxy, a trifluoromethyl or trifluoromethoxy group, and a group $S(O)_n$Alk;

$R_5$ represents a hydrogen atom or a $(C_1-C_4)$alkyl;

$R_6$ represents a $C_1-C_4$ alkyl;

$R_7$ and $R_8$ represent each independently a hydrogen atom or a $(C_1-C_4)$alkyl;

n represents 0, 1 or 2;

Alk represents a $(C_1-C_4)$alkyl; and with the proviso that when X represents a group —CO— or —CONR$_5$—, $R_2$ is other than:
- a $C_4-C_7$ non-aromatic carbocyclic radical, which is unsubstituted or substituted one or more times with a $(C_1-C_4)$alkyl;
- a phenyl, which is unsubstituted or substituted one or more times with substituents independently chosen from a halogen atom, a $(C_1-C_4)$alkyl, a hydroxyl, a $(C_1-C_4)$alkoxy, a cyano, a trifluoromethyl group and a group $CO_2R_6$ or $CONR_7R_8$; or from a 1-pyrrolyl or 1-pyrazoyl radical, the said radicals being unsubstituted or substituted one or more times with a $(C_1-C_4)$alkyl;
- a 1,2,3,4-tetrahydronaphthyl, which is unsubstituted or substituted one or more times with a $(C_1-C_4)$alkyl;
- a pyrrolyl, imidazolyl, pyridyl, pyrazolyl, furyl or thienyl radical, the said radicals being unsubstituted or substituted with one or more substituents independently chosen from a halogen atom, a $(C_1-C_4)$alkyl and a trifluoromethyl group;
- an indolyl, which is unsubstituted or substituted one or more times with substituents independently chosen from a halogen atom and a $(C_1-C_4)$alkyl;
- a benzofuryl, which is unsubstituted or substituted one or more times with substituents independently chosen from a halogen atom and a $(C_1-C_4)$alkyl; and
- a 2,1,3-benzoxadiazolyl;

or a salt thereof.

2. The compound of formula (I) according to claim 1, wherein —X— represents —CO— or a salt thereof.

3. The compound of formula (I) according to claim 1, wherein —X— represents —SO$_2$— or a salt thereof.

4. The compound of formula (I) according to claim 1, wherein —X— represents —CON(R$_5$)— or a salt thereof.

5. The compound of formula (I) according to claim 1, wherein —X— represents —CSN(R$_5$)— and wherein R$_5$ is as defined in claim 1; or a salt thereof.

6. A process for preparing a compound of formula (I) according to claim 1, comprising:

reacting a compound of formula (II):

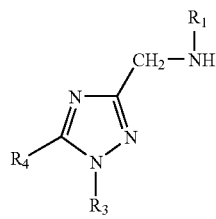

(II)

wherein R$_1$, R$_3$ and R$_4$ are as defined in claim 1, either with an acid of formula (III) or a functional derivative thereof:

HOOC—R$_2$ (III)

wherein R$_2$ is as defined in claim 1, to form a compound of formula (I) in which —X— represents —CO—;

or with a sulfonyl halide of formula (IV):

Hal-SO$_2$—R$_2$ (IV)

wherein R$_2$ is as defined in claim 1 and Hal represents a halogen atom, to form a compound of formula (I) in which —X— represents a group —SO$_2$—;

or with a haloformate of formula (V):

HalCOOAr (V)

wherein Hal represents a halogen atom and Ar represents a phenyl or a 4-nitrophenyl, to obtain an intermediate compound of formula (VI):

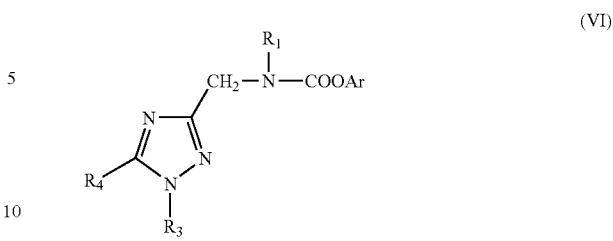

(VI)

wherein R$_1$, R$_3$ and R$_4$ are as defined in claim 1, which is then reacted with an amine of formula (VII):

HN(R$_5$)R$_2$ (VII)

wherein R$_2$ and R$_5$ are as defined in claim 1, to form a compound of formula (I) in which —X— represents —CON(R$_5$)—;

or with an isothiocyanate, R$_2$N=C=S (VIII), to form a compound of formula (I) in which —X— represents —CSNH—.

7. A pharmaceutical composition comprising a compound of formula (I) according to claim 1 or a pharmaceutically acceptable salt thereof in combination with at least one pharmaceutically acceptable excipient.

8. A pharmaceutical composition comprising a compound of formula (I) according to claim 2 or a pharmaceutically acceptable salt thereof in combination with at least one pharmaceutically acceptable excipient.

9. A pharmaceutical composition comprising a compound of formula (I) according to claim 3 or a pharmaceutically acceptable salt thereof in combination with at least one pharmaceutically acceptable excipient.

10. A pharmaceutical composition comprising a compound of formula (I) according to claim 4 or a pharmaceutically acceptable salt thereof in combination with at least one pharmaceutically acceptable excipient.

11. A pharmaceutical composition comprising a compound of formula (I) according to claim 5 or a pharmaceutically acceptable salt thereof in combination with at least one pharmaceutically acceptable excipient.

* * * * *

UNITED STATES PATENT AND TRADEMARK OFFICE
CERTIFICATE OF CORRECTION

| | | |
|---|---|---|
| PATENT NO. | : 7,781,471 B2 | Page 1 of 1 |
| APPLICATION NO. | : 12/125297 | |
| DATED | : August 24, 2010 | |
| INVENTOR(S) | : Francis Barth et al. | |

It is certified that error appears in the above-identified patent and that said Letters Patent is hereby corrected as shown below:

On the Title Pg, Item (54), in "Title", line 1, delete "DIARYL TRIAZOLMETHYLAMINE" and insert -- DIARYLTRIAZOLMETHYLAMINE --, therefor.

In column 1, line 1, delete "DIARYL TRIAZOLMETHYLAMINE" and insert -- DIARYLTRIAZOLMETHYLAMINE --, therefor.

In column 5, line 65, delete "$R_5$=H" and insert -- $R_5$=H --, therefor.

In column 7, line 62, delete "allyl" and insert -- alkyl --, therefor.

In column 11, line 11, delete "Y=O" and insert -- Y=O --, therefor.

In column 11, line 60, delete "—X—=—CO—" and insert -- —X=—CO— --, therefor.

In column 12, line 19-20, delete "—X—=—CONH—" and insert -- —X=—CONH— --, therefor.

In column 12, line 44, delete "—X—=—$SO_2$—" and insert -- —X=—$SO_2$— --, therefor.

In column 19, line 35, delete "Tourrette's" and insert -- Tourette's --, therefor.

In column 19, line 62-63, delete "rectional" and insert -- reactional --, therefor.

In column 22, line 33, in claim 1, delete "$C_1$-$C_4$" and insert -- ($C_1$-$C_4$) --, therefor.

Signed and Sealed this
Third Day of January, 2012

David J. Kappos
*Director of the United States Patent and Trademark Office*